United States Patent [19]

Bornack, Jr. et al.

[11] Patent Number: 4,894,433
[45] Date of Patent: Jan. 16, 1990

[54] WATER DISPERSIBLE POLYAMIDE DIETHANOLAMINE ESTER

[75] Inventors: Walter K. Bornack, Jr., Amherst; Roy C. Williams, Orchard Park, both of N.Y.; Keith R. McNally, Bedminster, N.J.

[73] Assignee: Union Camp Corporation, Wayne, N.J.

[21] Appl. No.: 152,638

[22] Filed: Feb. 5, 1988

[51] Int. Cl.[4] .............................................. C08G 63/02
[52] U.S. Cl. ..................... 528/272; 528/288; 528/291; 528/295.3; 528/295.5; 528/296; 528/302; 528/306; 528/308; 528/335; 528/338; 106/20; 106/27
[58] Field of Search ............ 528/272, 288, 291, 295.3, 528/295.5, 296, 302, 306, 308, 335, 338; 106/20, 27

[56] References Cited

U.S. PATENT DOCUMENTS

| | | | |
|---|---|---|---|
| 3,377,303 | 4/1968 | Peerman et al. | 528/339.3 |
| 3,484,339 | 12/1969 | Caldwell | 161/231 |
| 3,776,865 | 12/1973 | Glaser et al. | 528/339.3 |
| 3,778,394 | 12/1973 | Lovald et al. | 528/339.5 |
| 4,514,540 | 4/1985 | Peck | 524/514 |
| 4,683,262 | 7/1987 | Whyzmuzis et al. | 524/608 |

*Primary Examiner*—Morton Foelak
*Assistant Examiner*—S. A. Acquah
*Attorney, Agent, or Firm*—Michael L. Dunn

[57] ABSTRACT

The present invention comprises a water dispersible polyamide diethanolamine ester, having the following general structure:

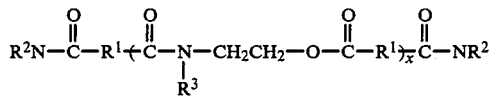

wherein x is an integer of 0-5; $R^1$ is independently at each occurrence an aliphatic group of up to 40 carbon atoms or polyamide segment; $R^2$ is independently at each occurrence

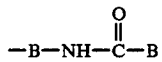

(where B is an aliphatic group of up to 10 carbon or

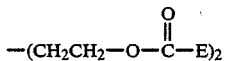

where E is an aliphatic group of up to 10 carbon atoms or the residue of a cyclic carboxylic anhydride bearing at least one free carboxyl group;

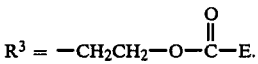

The product polyamide resin of the present invention comprises a mixture of monobasic and polybasic carboxylic acids, polyamines, DEA and cyclic carboxylic anhydrides. These resins may be used in various compositions including inks and laminates.

12 Claims, No Drawings

WATER DISPERSIBLE POLYAMIDE DIETHANOLAMINE ESTER

BACKGROUND OF THE INVENTION

There are a large variety of inks which are available for use on surfaces, such as metal, fabrics, wood, glass or plastics. Inks in general consist of a vehicle, or carrying agent, and a colorant that is evenly dispersed throughout the vehicle. One particular example of a type of ink is flexographic inks (formerly named aniline inks) which are used on presses with rubber printing plates. Flexographic inks are being used increasingly, especially for package wrappings such as foils, transparent plastic films, or paper-bag machines. They are generally composed of volatile solvents such as low boiling point alcohols, esters, aliphatic and aromatic hydrocarbons, ketones and water.

The most widely used family of flexographic inks are formulated from polyamide resins. Polyamides are formed by combining carboxylic acids, mostly dibasic, with organic polyamines, usually diamines. The acid and amine groups immediately react to form a salt. Upon heating to 140° C. or higher, this salt decomposes with the evolution of water to give an amide bond.

Alcohol soluble polyamides are widely used in alcohol based flexographic inks for printing on plastic film. Environmental concern over the amounts of volatile organic solvents in the atmosphere has led to a desire to use aqueous solutions that have less volatile organic solvents contained therein. In order to meet new Environmental Protection Agency regulations, it is desirable to employ water based flexographic inks with reduced levels of volatile organic solvents. In order to accommodate the reduced levels of volatile organic solvents, the polyamide resins used should have increased water solubility and yet retain other desirable properties of polyamide resins. The major technological difficulty has been in making water dispersible (WD) polyamides which provide inks with good properties such as adhesion, gloss, water resistance, and blocking resistance.

To achieve water dispersibility, it is necessary that the polyamide have a high acid value (AV) in the range of 50-100. When the free acid groups of the resin are neutralized with ammonia, it becomes water soluble. After printing, the ammonia evaporates and the resin develops water resistance.

Making a high AV polyamide using standard synthetic methods presents no problem. It is simply a matter of using a large excess of carboxylic acid over amine in the formulation. The difficulty is that polymer molecular weight is inversely proportional to AV. Therefore, if standard synthetic methods are used, WD polyamides with AV=50-100 are much lower in molecular weight than conventional alcohol soluble polyamides, which usually have acid values of less than 10. This lower molecular weight results in soft, sticky resins with degraded performance. Therefore, the problem is synthesizing polyamides with both high AV and good hardness.

Polyamides which are rendered water dispersible have been described in the prior art literature:

U.S. Pat. No. 3,776,865 to Glaser and Lovald discloses polyamide resins obtained by reacting an acid component comprised of a polymeric fat acid and another dicarboxylic acid with an amine component comprising isophorone diamine or mixtures thereof with an alkylene diamine. At least 12.5 carboxyl equivalent percent of the polymeric fat acid is employed. The patentees disclose that these resins are useful as binders applied by aqueous systems, particularly in flexographic/gravure inks where water reducibility is desired.

U.S. Pat. No. 3,778,394 to Lovald and Glaser discloses that the acid used to make the water dispersible polyamide is largely composed of a rosin acid-carboxylic acid adduct.

U.S. Pat. No. 4,514,540 to Peck, discloses that included in the starting materials of the water dispersible polyamide is a preformed synthetic resin having carboxyl and/or hydroxyl groups.

U.S. Pat. No. 4,683,262 Whyzmuzis and Menke discloses a method where little or no polymeric fatty acids are used to make the polyamide.

In spite of the wide variety of polyamide containing water dispersible compositions known through the prior art descriptions, there remains a need for improved polyamide compositions which are water dispersible and yet retain the properties of adhesion, gloss, water resistance and blocking

SUMMARY OF THE INVENTION

The present invention relates to the use of diethanolamine (DEA) in polyamide synthesis. A general formula for the product resin of the present invention is as follows:

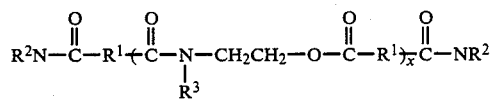

wherein x is an integer of 0-5; $R^1$ independently at each occurrence an aliphatic group of up to 40 carbon atoms or polyamide segment; $R^2$ independently at each occurrence

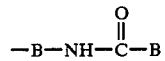

(where B is an aliphatic group of up to 10 carbon atoms) or

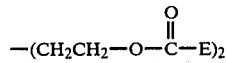

where E is an aliphatic group of up to 10 carbon atoms or the residue of a cyclic carboxylic anhydride bearing at least one free carboxyl group;

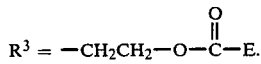

These resins may be used in making various inks, including inks for both surface printing and laminate printing.

DETAILED DESCRIPTION OF THE INVENTION

In standard polyamide synthesis, carboxylic acids, usually dibasic, are mixed with amines, usually difunctional. An amine salt immediately forms. When heated above 140° C., this salt decomposes with the evolution of water to give an amide. Usually, the number of acid groups and amine groups in the starting formulation are approximately equal. Therefore, the final polyamide has AV and amine value (AmV) near 0. Acid value as used in the art is defined as the number of milligrams of potassium hydroxide required to neutralize the free acids present in 1 gram of resin. Amine value as used in the art is defined as the milligrams of potassium hydroxide equivalent to the free amine groups in 1 gram of the polyamide resin so it is analogous to AV.

The amines normally used in polyamide synthesis are ethylene diamine (EDA), hexamethylene diamine (HMDA), 1,2-diaminocyclohexane (DCH), isophorone diamine (IPDA), and m-xylene diamine (MXDA). The amines normally used in polyamide synthesis are partially replaced with DEA and resins are made which are similar in hardness to conventional alcohol soluble polyamides. In addition, treatment of these DEA containing resins with cyclic anhydrides gives products with AV 50-100 which are water dispersible. Therefore, the present invention discloses a polyamide with both high AV and good hardness.

In the DEA containing formulation of the present invention, the number of amine groups is also approximately equal to the number of acid groups. However, there are also present the hydroxyl groups of the DEA, which can react with the acid groups to form esters. The combined amine and hydroxyl groups are in excess over the acid groups. In competition for the acid groups, the amines are the more reactive so that when the polymer formation is complete and the acid value is near 0, only about 20% of the hydroxyl groups initially present have been esterified. Upon treatment with cyclic anhydrides, the free hydroxyl groups open the anhydride ring to form the half ester. The cyclic anhydrides which may be used are anhydrides which contain one anhydride ring per molecule. Examples of cyclic carboxylic anhydrides which may be used are trimellitic anhydride (TMA), tetrahydrophthalic anhydride (THPA), phthalic anhydride, succinic anhydride and dodecenyl succinic anhydride (DDSA). The free carboxyl groups that are created provide the water dispersibility.

This anhydride treatment must occur after the resin has been formed and most of the amine groups have reacted. This is because a primary amine readily reacts with the five-membered anhydride ring to give the five-membered imide ring, which has no free carboxyl group.

A general composition of the invention comprises a reaction product of a mixture of about 50-70 weight percent polybasic carboxylic acids; about 3-10 weight percent monobasic carboxylic acids; about 5-10 weight percent DEA; about 5-15 weight percent polyamines; reacted with about 5-25 weight percent cyclic carboxylic anhydrides.

A general synthesis schematic may be as follows:

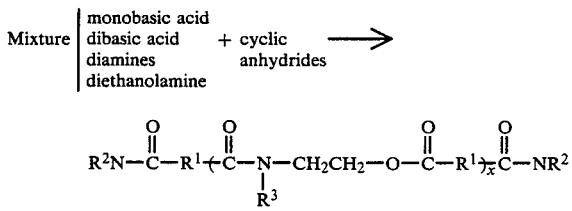

wherein x is an integer of 0-5; $R^1$ is independently at each occurrence an aliphatic group of up to 40 carbon atoms or polyamide segment; $R_2$ is independently at each occurrence

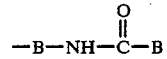

(where B is an aliphatic group of up to 10 carbon atoms)

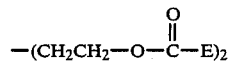

where B is an aliphatic group of up to 10 carbon atoms or the residue of cyclic carboxylic anhydride bearing at least one free carboxyl group;

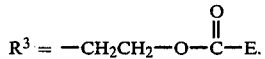

Polyamides in general are formed by combining carboxylic acids with organic polyamines. Polyamines employed in the present invention are organic amines having polyamine functionality and handling properties such as appropriate viscosity to permit use in accordance with the present invention. Especially suitable are one or more of the aliphatic or cycloaliphatic diamines such as those of the formula:

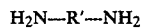

wherein R' is an aliphatic or cycloaliphatic hydrocarbon radical. Preferred diamines are hexamethylene diamine (HMDA), m-xylene diamine (MXDA), 1,2-diaminocyclohexane (DCH), isophorone diamine and ethylene diamine (EDA). In addition, diethylene triamine may also be used.

The carboxylic acids may be either monobasic or dibasic. Monobasic as used in the art are acids having one displaceable hydrogen atom per molecule. Dibasic as used in the art are acids having two displaceable hydrogen atoms per molecule. Examples of monobasic acids which may be used are propionic acid and acetic acid. Examples of dibasic acids which may be used are dimer acids and Westvaco Diacid 1550. Westvaco Diacid 1550 (WV 1550) is a dibasic adduct of acrylic acid and a fatty acid and is essentially 2-n-hexyl-5-(7-carboxyl-n-heptyl)-cyclohex-3-ene carboxylic acid. Dimer acid as used herein is defined as a complex mixture resulting from the polymerization of fatty acids. Representative of these Dimer acids are those that are commercially available from the polymerization of tall oil fatty acids. These have a typical composition as follows:

| | % by weight |
|---|---|
| $C_{18}$ monobasic acids (monomer) | 0-5 |
| $C_{36}$ dibasic acids (dimer) | 60-95 |
| $C_{54}$ and higher polybasic acids (trimer) | 1-35 |

The relative ratios of monomer, dimer and trimer are dependent on the nature of the starting material and the conditions of polymerization. The preferred compositions for the present invention are those that comprise about 82% dimer and 18% trimer.

The polyamide compositions of the invention comprise the conventional components of polyamides namely, monobasic and/or polybasic derivatives of fatty acids, including dibasic derivatives such as dimer acid and 2-n-hexyl-5-(7-carboxyl-n-heptyl)-cyclohex-3-ene carboxylic acid as well as various polyamines including diamines, such as isophorone diamine (IPDA), m-xylene diamine (MXDA), ethylene diamine (EDA), hexamethylene diamine (HMDA), 1,2-diamino cyclohexane (DCH) and 2-methylpentamethylene diamine. In addition, the reaction mixtures may also include a variety of inert, non-reactive ingredients such as anti-oxidants, acidic catalysts, antifoam agents and the like. Further, small amounts of other low molecular weight dibasic acids, such as adipic acid, may be included.

The following descriptions of the invention are not intended to be limiting in any manner, they are merely illustrative. Various modifications, applications and changes may occur to those skilled in the art without departing from the true spirit and scope of the invention.

Resin Synthesis

The apparatus is a 5-liter flask equipped with a mechanical stirrer, a nitrogen inlet, a thermometer, and a water trap. Dimer acid (1284 rams), WV 1550 (448 grams), propionic acid (210 grams), and a trace of silicone antifoam are charged to the flask, blanketed with nitrogen, and heated to 70° C. DEA (275 grams) is then added, followed by a mixture of IPDA (114 grams) and EDA (170 grams). This latter addition is carried out slowly so that the temperature remains below 130° C. The mixture is stirred at 120°–130° C. for 15 minutes. Then it is heated to 180° C., distilling off the water of reaction. The resin melt is maintained at 180° C. until the AV drops below 3, which usually takes 1–2 hours. It is then cooled to 170° C. and tetrahydrophthalic anhydride (THPA, 488 grams) is added. The melt is maintained at 170° C. for 1.5 hours and then discharged.

The product resin typically has the following properties:

| | |
|---|---|
| AV | 50–55 |
| AmV | 5–10 |
| Softening Point (R&B) | 105–110° C. |
| Solution Viscosity (60% in n-propanol) | 5–10P |

Neutralization of the 60% nonvolatile (NV) n-propanol solution with ammonia and dilution with water to 30% NV gives a clear solution with a viscosity of 1–2 P (poise). Softening Point as used herein is the Ring and Ball (R & B) softening point. The product resin as disclosed above is designated herein as EA-5748. This example is essentially repeated except that percentages of components are varied. Preferred resulting resins are shown in Table I, hereunder.

Water-Based Flexographic Ink Formulation

A resin solution is prepared by charging the following into a blender: n-propanol (22.0 grams); water (51.5 grams); ammonium hydroxide (1.5 grams); and EA-5748 polyamide (25.0 grams). The components are mixed until a clear, particle-free solution is obtained, which usually occurs within 15 minutes. The pH is adjusted to 8.2–8.9 with ammonium hydroxide.

A blue ink was prepared by adding 28.0 grams of an organic pigment dispersion (40–50% pigment) to the above resin solution (54.0 grams). The ink was reduced to a viscosity of 20 seconds (on a No. 2 Zahn cup) by the addition of isopropanol (1 gram) and water (15 grams).

Prints made with this ink on corona treated polypropylene film had gloss, adhesion, and scratch resistance equal to an alcohol soluble polyamide. Water and blocking resistance were slightly poorer but still acceptable. Drying time was slightly longer.

These inks as prepared according to the present invention may also be used in laminating applications with both water-base and solvent-based adhesives. More specifically, they can be used in both polypropylene/polypropylene and polypropylene/foil laminates. When used in the above manner, destructive bonds develop within about one week. Destructive bonds as known in the art are bonds which are formed when the two layers of the laminate cannot be separated without tearing of the laminate.

Preferred Compositions

The following are some preferred compositions for the DEA polyamides:

TABLE I

| | EA-5696 Wt % | EA-5748 Wt % | EA-5766 Wt % |
|---|---|---|---|
| Dimer acid | 65.94 | 42.89 | 32.48 |
| WV 1550 | — | 14.98 | 22.70 |
| Adipic Acid | — | — | 2.22 |
| Propionic aid | 5.17 | 7.00 | 3.74 |
| IPDA | 3.93 | 3.80 | 3.67 |
| EDA | 5.83 | 5.69 | 5.26 |
| DEA | 6.57 | 9.18 | 8.67 |
| TMA | 7.00 | — | 14.57 |
| THPA | 5.56 | 16.46 | — |
| DDSA* | — | — | 6.69 |

*Dodecenyl succinic anhydride

What is claimed is:

1. A composition comprising the formula:

$$R^2N-\overset{O}{\underset{\|}{C}}-R^1+\overset{O}{\underset{\|}{C}}-\underset{R^3}{N}-CH_2CH_2-O-\overset{O}{\underset{\|}{C}}-R^1\overline{)_x}\overset{O}{\underset{\|}{C}}-NR^2$$

wherein x is an integer of 0–5; $R^1$ is independently at each occurrence an aliphatic group of up to 40 carbon atoms or polyamide segment; $R^2$ is independently at each occurrence $$-B-NH-\overset{O}{\underset{\|}{C}}-B$$

(where B is an aliphatic group of up to 10 carbon atoms) or $$-(CH_2CH_2-O-\overset{O}{\underset{\|}{C}}-E)_2$$

where E is an aliphatic group of up to 10 carbon atoms or the residue of a cyclic carboxylic anhydride bearing at least one free carboxyl group;

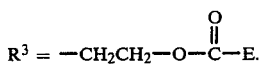

2. A composition comprising a reaction product of:
(a) a mixture of about 50–70 weight percent polybasic carboxylic acids; about 3–10 weight percent monobasic carboxylic acids; about 5–10 weight percent DEA; about 5–15 weight percent polyamines; and
(b) about 5–25 weight percent cyclic carboxylic anhydrides.

3. The composition of claim 2 wherein the polybasic carboxylic acids comprise dibasic acids.

4. The composition of claim 3 wherein the dibasic acids may be a Dimer acid or a Dimer acid in combination with 2-n-hexyl-5-(7-carboxyl-n-heptyl)-cyclohex-3-ene carboxylic acid.

5. The composition of claim 2 wherein the monobasic carboxylic acid is propionic acid.

6. The composition of claim 2 wherein the polyamines comprise at least one of EDA, HMDA, IPDA, MXDA, DCH, 2-methylpentamethylene diamine or diethylene triamine.

7. The composition of claim 2 wherein the cyclic carboxylic anhydrides contain one anhydride ring per molecule.

8. The composition of claim 7 wherein the cyclic carboxylic anhydride comprises at least one of TMA, THPA or DDSA.

9. An ink formulation comprising the composition of claim 2, wherein the composition has a softening point of between about 90° C. and 140° C.

10. A laminate comprising the composition of claim 2.

11. An aqueous dispersion comprising the composition of claim 1.

12. An aqueous dispersion comprising the composition of claim 2.

* * * * *